United States Patent

Nagano et al.

[11] Patent Number: 4,622,063
[45] Date of Patent: Nov. 11, 1986

[54] 4-(2-FLUORO-4-HALO-5-SUBSTITUTED PHENYL)URAZOLS, AND HERBICIDAL USE

[75] Inventors: Eiki Nagano, Nishinomiya; Shunichi Hashimoto, Toyonaka; Ryo Yoshida, Kawanishi; Hiroshi Matsumoto, Toyonaka; Katsuzo Kamoshita, Osaka, all of Japan

[73] Assignee: Sumitomo Chemical Company, Limited, Osaka, Japan

[21] Appl. No.: 592,064

[22] Filed: Mar. 22, 1984

Related U.S. Application Data

[62] Division of Ser. No. 418,426, Sep. 15, 1982, Pat. No. 4,452,981.

[30] Foreign Application Priority Data

Sep. 19, 1981 [JP] Japan .................. 56-148443
Feb. 19, 1982 [JP] Japan .................. 57-26512

[51] Int. Cl.$^4$ .................. A01N 43/653; C07D 487/04
[52] U.S. Cl. .................. 71/92; 540/568
[58] Field of Search .................. 260/245.5; 71/92

[56] References Cited

U.S. PATENT DOCUMENTS 4,213,773  7/1980  Wolf .................. 71/92
4,214,891  7/1980  Wolf .................. 71/92
4,235,905  11/1980  Morrison et al. .................. 544/236
4,249,934  2/1981  Wakabayashi et al. .................. 548/264
4,404,019  9/1983  Hematsu et al. .................. 548/263

FOREIGN PATENT DOCUMENTS 53-44587  4/1978  Japan .................. 544/236

OTHER PUBLICATIONS

Wakabanashi et al; Kokai 77-83552, Chem. Abstracts 88:50904k (1978).
Kornet et al., Chem. Abstracts 95:62107k (1981).

*Primary Examiner*—Alton D. Rollins
*Attorney, Agent, or Firm*—Birch, Stewart, Kolasch & Birch

[57] ABSTRACT

A condensed phenylurazol of the formula:

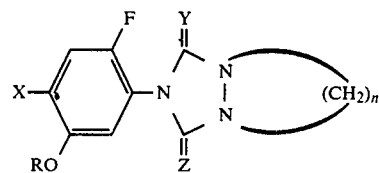

wherein X is a chlorine atom or a bromine atom, Y and Z are each an oxygen atom or a sulfur atom and R is a $C_1$–$C_3$ alkyl group, an allyl group or propargyl group and n is an integer of 4 or 5, which is useful as a herbicide.

19 Claims, No Drawings

4-(2-FLUORO-4-HALO-5-SUBSTITUTED PHENYL)URAZOLS, AND HERBICIDAL USE

This application is a divisional of copending application Ser. No. 418,426 filed on Sept. 15, 1982, now U.S. Pat. No. 4,452,981, issued June 5, 1984.

The present invention relates to 4-(2-fluoro-4-halo-5-substituted phenyl)urazols bearing a condensed hexahydropyridazine or hexahydrodiazepine ring (hereinafter referred to as "the condensed phenylurazol(s)"), and their production and use.

The said condensed phenylurazols are representable by the formula:

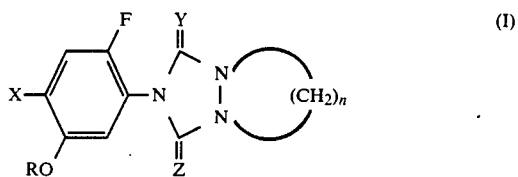

wherein X is a chlorine atom or a bromine atom, Y and Z are each an oxygen atom or a sulfur atom, R is a $C_1$-$C_3$ alkyl group, an allyl group or a propargyl group and n is an integer of 4 or 5.

It is known that some 4-phenylurazols exhibit a herbicidal activity. For instance, U.S. Pat. No. 4,249,934, Japanese Patent Publication (unexamined) No. 44587/1978, etc. disclose that 2-(4-chlorophenyl-5,6,7,8-tetrahydro-1H-[1,2,4]triazolo[1,2-a]pyridazine-1,3(2H)-dione, 2-(4-chloro-2-fluorophenyl)-5,6,7,8-tetrahydro-1H-[1,2,4]triazolo[1.2-a]pyridazine-1,3(2H)-dione, 2-(4-chlorophenyl)-1H,5H-[1,2,4]triazolo[1,2-a][1,2]diazepin-1,3(2H)dione, etc. show a herbicidal activity. However, their herbicidal effect is not always satisfactory.

It has been found that the condensed phenylurazols (I) show a strong herbicidal activity against a wide variety of weeds including Graminaceous weeds, Cyperaceae weeds and broad-leaved weeds at small doses and do not produce any material phytotoxicity on various agricultural crops (e.g. corn, soybean, cotton, wheat). Examples of Graminaceous weeds against which the condensed phenylurazols (I) show a herbicidal activity are barnyardgrass (*Echinochloa crus-galli*), green foxtail (*Setaria viridis*), large crabgrass (*Digitaria sanguinalis*), Johnsongrass (*Sorghum halepense*), wild oat (*Avena fatua*), black grass (*Alopecurus myosuroides*), goosegrass (*Eleusine indica*), annual bluegrass (*Poa annua*), bermudagrass (*Cynodon dactylon*), quackgrass (*Agropyron repens*), etc. Examples of broad-leaved weeds are tall morningglory (*Ipomoea purpurea*), velvetleaf (*Abutilon theophrasti*), sicklepod (*Cassia obtusifolia*), wild sunflower (*Helianthus annus*), cocklebur (*Xanthium pensylvanicum*), wild mustard (*Brassica kaber*), common chickweed (*Stellaria media*), common purslane (*Portulaca oleracea*), jimsonweed (*Datura stramonium*), hemp sesbania (*Sesbania exaltata*), sun spurge (*Euphorbia helioscopia*), black nightshade (*Solanum nigrum*), prickly sida (*Sida spinosa*), common ragweed (*Ambrosia artemisiifolia*), smartweed sp. (Polygonum sp.), redroot pigweed (*Amaranthus retroflexus*), bedstraw (*Galium aparine*), pineappleweed (Matricaria spp.), birdseye speedwell (*Veronica persica*), wild buckwheat (*Polygonum convolvulus*), beggarticks (Bidens spp.), common lambsquarters (*Chenopodium album*), bindweed (*Calystegia japonica*), monochoria (*Monochoria vaginalis*), Dopatrium junceum, waterwort (*Elatine triandra*), false pimpernel (*Lindernia procumbens*), toothcup (*Rotala indica*), arrowhead (*Sagittaria pygmaea*), etc. Examples of Cyperaceae weeds are nutsedge sp. (*Cyperus microiria*), purple nutsedge (*Cyperus rotundus*), yellow nutsedge (*Cyperus esculentus*), hardstem bulrush (*Scirpus juncoides*), nutsedge (*Cyperus serotinus*), water chestnut (*Eleocharis kuroguwai*), slender spikerush (*Eleocharis acicularis*), etc. Accordingly, the condensed phenylurazols (I) can be used as herbicides applicable to paddy fields as well as to an agricultural plowed field. They are also useful as herbicides to be employed for a crop field, orchard, tea garden, mulberry field, rubber plantation, forest, lawn, pasture, non-agricultural field, etc.

The condensed phenylurazols (I) can be produced by various procedures, among which typical examples are shown below:

PROCEDURE A

The condensed phenylurazols of the formula (I) wherein at least one of Y and Z is an oxygen atom can be produced by reacting a phenylurazol of the formula:

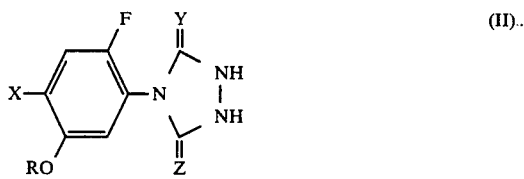

wherein X, Y, Z and R are each as defined above but at least one of Y and Z is an oxygen atom with a dihaloalkane of the formula:

$$A-(CH_2)_n-A' \qquad (III)$$

wherein A and A' are each a halogen atom (e.g. chlorine, bromine) and n is as defined above, usually in an inert solvent (e.g. dimethylformamide, dimethylsulfoxide, acetonitrile, ethylene glycol monomethyl ether, tetrahydrofuran, diethyl ether) at a temperature of $-80°$ to $200°$ C.

Preferably, the phenylurazol (II) is previously metallized, and the metallized phenylurazol is subjected to reaction with the dihaloalkane (III). The metallization may be achieved by treatment of the phenylurazol (II) with a metallizing agent (e.g. sodium alkoxide, sodium hydride, n-butyl lithium) in an inert solvent (e.g. methanol, ethanol, diethyl ether, tetrahydrofuran) at a temperature of $-80°$ to $160°$ C. The thus produced metallized phenylurazol can be subjected to reaction with the dihaloalkane (III) as above with or without its isolation from the reaction mixture.

PROCEDURE B

The condensed phenylurazols of the formula (I) wherein Z is an oxygen atom and n is an integer of 4 can be produced by treatment of a urea of the formula:

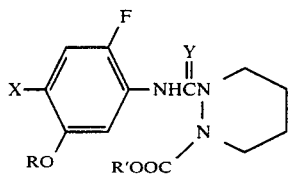

(IV)

wherein R' is a lower alkyl group (e.g. methyl, ethyl, n-propyl, isopropyl) and X, Y and R are each as defined above with a base (e.g. sodium methoxide, sodium hydroxide, potassium hydroxide) in an inert solvent (e.g. water, toluene, benzene, methanol, ethanol) at a temperature of 0° to 200° C.

PROCEDURE C

The condensed phenylurazols of the formula (I) wherein Z is an oxygen atom and n is an integer of 4 can be produced by reacting a urea of the formula:

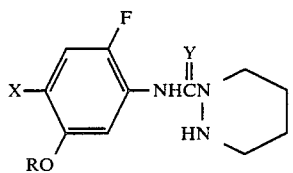

(V)

wherein X, R and Y are each as defined above with phosgene in an inert solvent (e.g. toluene, tetrahydrofuran, 1,4-dioxane) at a temperature of from 0° C. to the boiling temperature of the solvent. When desired, a base (e.g. triethylamine, pyridine, diethylaniline) may be present in the reaction system.

PROCEDURE D

The condensed phenylurazols of the formula (I) wherein Z is a sulfur atom and n is an integer of 4 can be produced by reacting a urea of the formula:

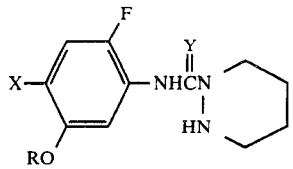

(V)

wherein X, R and Y are each as defined above with carbon disulfide in an inert solvent (e.g. methanol, ethanol, tetrahydrofuran) in the presence of a base such as an alkali metal hydroxide (e.g. sodium hydroxide, potassium hydroxide) or a tertiary amine (e.g. pyridine, triethylamine).

PROCEDURE E

The condensed phenylurazols of the formula (I) wherein Y and Z are each a sulfur atom can be produced by reacting the corresponding condensed phenylurazol of the formula (I) wherein Y and Z are each an oxygen atom with phosphorus pentasulfide in an inert solvent (e.g. xylene, toluene, hexane) at the boiling temperature of the solvent.

The production of the starting materials is summarized in the following scheme:

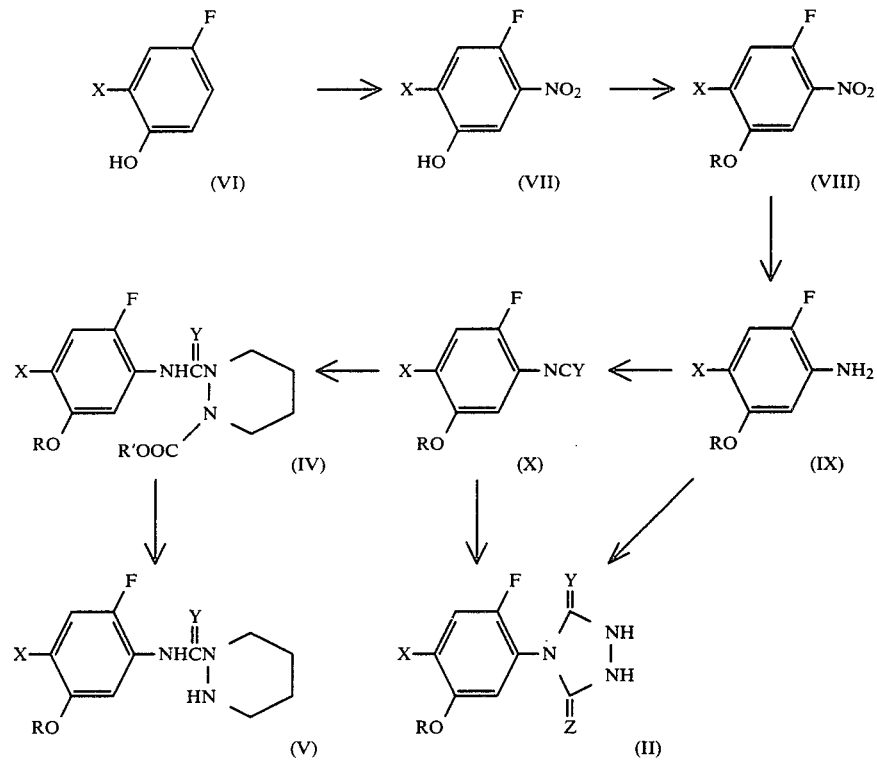

wherein X, Y, Z, R and R' are each as defined above.

Namely, the phenol (VI) is selectively nitrated to the nitrophenol (VII), which is subjected to alkylation, alkenylation or alkynylation. The resultant nitrobenzene (VIII) is subjected to reduction, and the resulting aniline (IX) is reacted with phosgene or thiophosgene to give the isocyanate or isothiocyanate (X), which is reacted with an N-alkoxycarbonylhexahydropyridazone to give the urea (IV). Hydrolysis and decarboxylation of the urea (IV) give the urea (V). The above aniline (IX) is reacted with a 2-alkoxycarbonylhydrazinecarbonyl chloride, followed by cyclization with a base to give the phenylurazol (II). Alternatively, the phenylurazol (II) can be produced by reacting the isocyanate or isothiocyanate (X) with an alkoxycarbonylhydrazine, followed by cyclization with a base.

Explaining the above conversions more in detail, the nitration of the phenol (VI) to the nitrophenol (VII) may be accomplished by application of a per se conventional nitration procedure to the former. Usually, however, the indirect nitration which consists of the following three steps is favorable in achievement of the selective nitration at the desired position:

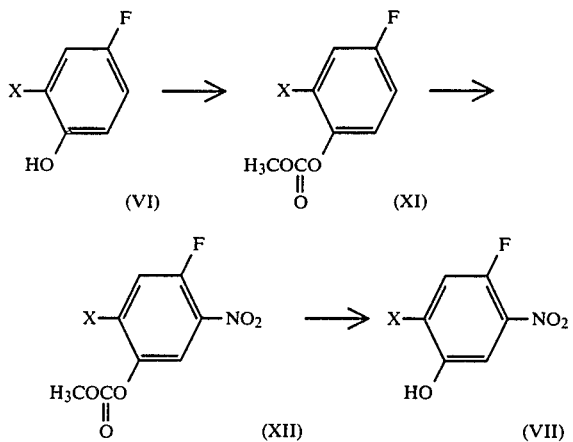

wherein X is as defined above. Thus, the phenol (VI) (Finger et al.: J. Am. Chem. Soc., 81, 94 (1959)) is converted into its alkali metal salt by treatment with an aqueous solution of an alkali metal hydroxide (e.g. sodium hydroxide, potassium hydroxide), and the resulting salt is reacted with an alkyl haloformate such as methyl chloroformate in water at a temperature of 0° to 10° C. The thus prepared carbonic ester (XI) is nitrated with a mixture of conc. sulfuric acid and conc. nitric acid at room temperature. Then, the nitrobenzene (XII) thus obtained is hydrolyzed with an aqueous alkaline solution such as an aqueous sodium hydroxide solution at a temperature of 40° to 80° C. to give the nitrophenol (VII).

The alkylation, alkenylation or alkynylation for conversion of the nitrophenol (VII) into the nitrobenzene (VIII) may be carried out by treatment of the former with an alkali metal carbonate (e.g. potassium carbonate), an alkali metal hydride (e.g. sodium hydride) or an alkali metal alkoxide (e.g. sodium methoxide) and reacting the resultant alkali metal salt with a halide of the formula: R-Q wherein Q is a halogen atom (e.g. chlorine, bromine, iodine) and R is as defined above in a polar solvent (e.g. water, dimethylformamide, acetonitrile, acetone, dimethylsulfoxide), usually at a temperature of 10° to 200° C., preferably of 30° to 100° C. The use of a phase transfer catalyst such as tetrabutylammonium bromide is favorable for smooth accomplishment of the reaction.

Reduction of the nitrobenzene (VIII) to the aniline (IX) may be achieved in various procedures. When, for instance, R in the compound (VIII) is $C_1$-$C_4$ alkyl, there may be adopted a per se conventional reduction procedure for converting a nitro group into an amino group wherein a reducing agent such as sodium sulfide or iron powder or catalytic reduction is employed. One of the typical procedures comprises introduction of a 3 molar amount of hydrogen into a reaction system comprising one molar amount of the compound (VIII) and a 1/10 to 1/100 molar amount of platinum dioxide at room temperature under atmospheric pressure. Another typical procedure comprises admixing an acetic acid solution containing one molar amount of the compound (VIII) with a 5 % acetic acid solution containing a 2.5 to 5.0 molar amount of iron powder such as reductive iron or electrolytic iron and effecting the reaction at a temperature of 80° to 100° C. When R in the compound (VIII) is propargyl or allyl, there may be adopted reduction with iron powder. For instance, an acetic acid solution containing one molar amount of the compound (VIII) may be admixed with a 5% acetic acid solution containing a 2.5 to 5.0 molar amount of iron powder such as reductive iron or electrolytic iron at a temperature of 80° to 120° C., preferably of 90° to 110° C., for a period of 0.5 to 5 hours.

The aniline (IX) is converted into the isocyanate or isothiocyanate (X) by reacting the former with phosgene or thiophosgene in an inert solvent (e.g. toluene, benzene, ethyl acetate, tetrahydrofuran, 1,4-dioxane).

The isocyanate or isothiocyanate (X) can be converted into the urea (IV) by reacting the former with an N-alkoxycarbonylhexahydropyridazine in an inert solvent (e.g. benzene, toluene, hexane, tetrahydrofuran), preferably in the presence of an organic base (e.g. pyridine, triethylamine), at a temperature from room temperature (ca. 20° C.) to the boiling temperature of the solvent.

Hydrolysis and decarboxylation of the urea (IV) by treatment with an aqueous alkaline solution at a temperature of 0° to 100° C. affords the urea (V).

Alternatively, the phenylurazol (II) can be produced by reacting the isocyanate or isothiocyanate (X) with an alkoxycarbonylhydrazine or alkoxythiocarbonylhydrazine in an inert solvent (e.g. toluene, chloroform, tetrahydrofuran) at a temperature of 0° to 100° C., followed by treatment of the resultant semicarbazide of the formula:

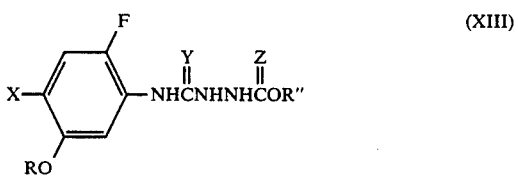

(XIII)

wherein R" is an alkyl group and X, Y, Z and R are each as defined above with an aqueous alkaline solution such as potassium hydroxide solution and then with a mineral acid (e.g. hydrochloric acid, sulfuric acid).

The above obtained aniline (IX) can be converted into the semicarbazide (XIII) by reacting the former with a 2-alkoxycarbonylhydrazinecarbonyl chloride in an inert solvent (e.g. benzene, toluene, diethyl ether, tetrahydrofuran, dioxane) at the boiling temperature of the solvent.

The above produced condensed phenylurazols (I) and their intermediates are, when desired, purified by a per se conventional procedure such as recrystallization or column chromatography.

Practical and presently preferred embodiments for production of the condensed phenylurazols (I) are shown in the following Examples.

EXAMPLE 1

To a solution of metallic sodium (0.7 g) in methanol (40 ml), 4-(4-chloro-2-fluoro-5-methoxy)urazol (3.87 g) was added, and the resultant mixture was concentrated under reduced pressure. A solution of 1,4-dibromobutane (3.5 g) in dimethylformamide (40 ml) was added thereto. The resulting mixture was stirred at 100° to 110° C. for 4 hours. After being allowed to cool to room temperature, water was added to the mixture, which was then extracted with ether. The ether layer was washed with water, dried and concentrated to give crystals. The crystals were washed with ether to give 1.26 g of 2-(4-chloro-2-fluoro-5-methoxyphenyl)-5,6,7,8-tetrahydro-1H-[1,2,4]triazolo[1,2-a]pyridazine-1,3(2H)-dione (Compound No. 1) as colorless crystals. M.P., 131°-132° C. IR $\nu_{max}$(cm$^{-1}$) 1770, 1720. NMR δ (ppm): 1.9 (4H, m), 3.6 (4H, m), 3.85 (3H, s), 6.85 (1H, d, J=6 Hz), 7.3 (1H, d, J=10 Hz).

EXAMPLE 2

To a solution of metallic sodium (0.46 g) in methanol (20 ml), 2-(4-chloro-2-fluoro-5-methoxyphenyl)urazol (2.6 g) was added, and the resultant mixture was concentrated under reduced pressure. The residue was dissolved in dimethylformamide (20 ml), 1,5-dibromopentane (2.3 g) was added thereto, and the resulting mixture was stirred at 100° to 120° C. for 4 hours. After being allowed to cool, water was added to the mixture, which was then extracted with ethyl acetate. The extract was washed with a saturated sodium chloride solution, dried over anhydrous magnesium sulfate and concentrated under reduced pressure. The residue was purified by silica gel column chromatography and recrystallized from methanol to give 0.42 g of 2-(4-chloro-2-fluoro-5-methoxyphenyl)-1H,5H-[1,2,4]triazolo[1,2-a][1.2]diazepine-1,3(2H)-dione (Compound No. 3). M.P., 121.5°-123° C. IR $\nu_{max}$(cm$^{-1}$) 1750, 1680. NMR δ (ppm): 1.8 (6H, m), 3.9 (3H, s).

EXAMPLE 3

Ethyl 2-[(4-chloro-2-fluoro-5-(1-methylethoxy)-phenyl)aminothioxomethyl]-3,4,5,6-tetrahydro-1(2H)-pyridazinecarboxylate (0.66 g) was dissolved in toluene (20 ml), and several drops of sodium methoxide were added thereto, followed by heating under reflux for 3 hours. Water was added to the resultant mixture, which was then extracted with toluene. The extract was washed with a saturated sodium chloride solution, dried and concentrated to give 0.3 g of 2-[4-chloro-2-fluoro-5-(1-methylethoxy)phenyl]-5,6,7,8-tetrahydro-1H-[1,2,4]triazolo[1,2-a]pyridazine-3-thioxo-1(2H)-one (Compound No. 15). $n_D^{25}$ 1.5720. IR $\nu_{max}$(cm$^{-1}$): 1740, 1490, 1250. NMR δ (ppm): 1.4 (6H, d), 2.0 (4H, m), 3.65 (2H, m), 4.0 (2H, m), 4.45 (1H, m), 6.9 (1H, d), 7.25 (1H, d).

EXAMPLE 4

2-(4-Bromo-5-ethoxy-2-fluorophenyl)-1H,5H-[1,2,4]triazolo[1,2-a][1,2]diazepine-1,3(2H)-dione (0.63 g) was dissolved in xylene (10 ml), and phosphorus pentasulfide (0.46 g) was added thereto, followed by heating under reflux for 8 hours. The reaction mixture was filtered to eliminate insoluble materials, and the filtrate was concentrated under reduced pressure. The residue was crystallized and washed with methanol to give 0.65 g of 2-(4-bromo-5-ethoxy-2-fluorophenyl)-1H,5H-[1,2,4]triazolo[1,2-a][1,2]diazepine-1,3(2H)-dithione (Compound No. 9). M.P., 173.5°-174.5° C. IR $\nu_{max}$ (cm$^{-1}$): NMR δ (ppm): 1.45 (3H, t), 1.9 (6H m), 4.07 (2H, q).

Some additional examples of the condensed phenylurazol (I) produced in the same manner as above are shown in Table 1.

TABLE 1

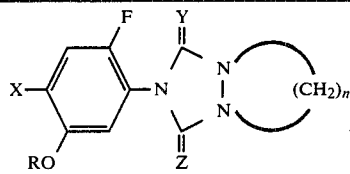

| Compound No. | X | Y | Z | n | R | Physical property |
|---|---|---|---|---|---|---|
| 1 | Cl | O | O | 4 | —CH₃ | M.P. 131–132° C. |
| 2 | Cl | S | O | 4 | —CH₃ | M.P. 146–147° C. |
| 3 | Cl | O | O | 5 | —CH₃ | M.P. 121.5–123° C. |
| 4 | Cl | S | S | 5 | —CH₃ | M.P. 229–231° C. |
| 5 | Br | O | O | 4 | —CH₃ | M.P. 162.5–164.5° C. |
| 6 | Cl | O | O | 4 | —CH₂CH₃ | M.P. 116–117° C. |
| 7 | Br | O | O | 4 | —CH₂CH₃ | M.P. 141–143° C. |
| 8 | Br | O | O | 5 | —CH₂CH₃ | M.P. 56–58° C. |
| 9 | Br | S | S | 5 | —CH₂CH₃ | M.P. 173.5–174.5° C. |
| 10 | Cl | O | O | 4 | —CH₂CH₂CH₃ | M.P. 97.5–99° C. |
| 11 | Cl | S | S | 4 | —CH₂CH₂CH₃ | M.P. 181.5–182.5° C. |
| 12 | Cl | O | O | 5 | —CH₂CH₂CH₃ | $n_D^{22.0}$ 1.5310 |
| 13 | Br | O | O | 4 | —CH₂CH₂CH₃ | M.P. 92–93° C. |
| 14 | Cl | O | O | 4 | —CH(CH₃)₂ | M.P. 140–142.5° C. |
| 15 | Cl | S | O | 4 | —CH(CH₃)₂ | $n_D^{25}$ 1.5720 |
| 16 | Cl | S | O | 4 | —CH₂CH=CH₂ | M.P. 58–63° C. |
| 17 | Br | O | O | 4 | —CH₂CH=CH₂ | M.P. 109–111° C. |
| 18 | Cl | S | O | 4 | —CH₂C≡CH | M.P. 148–150° C. |

EXAMPLE 5

A solution of 2-fluoro-4-chloro-5-n-propoxyphenyl isocyanate (1.8 g) in benzene (10 ml) was added to a toluene solution containing methoxycarbonylhydrazine (0.71 g), and the resultant mixture was allowed to stand overnight. The precipitated crystals were collected by filtration and dissolved in a 4M aqueous sodium hydroxide solution (10 ml) under heating. To the resulting solution, conc. hydrochloric acid was added, and the precipitated crystals were collected by filtration to give 2.6 g of 4-(4-chloro-2-fluoro-5-n-propoxyphenyl)urazol. M.P., 181°-182° C. IR $\nu_{max}$ (cm$^{-1}$): 3150, 1710, 1680. NMR δ (ppm): 1.1 (3H, t), 4.0 (3H, q), 7.0 (1H, d), 7.3 (1H, d)

Some examples of the phenylurazol (II) produced in the same manner as above are shown in Table 2.

TABLE 2

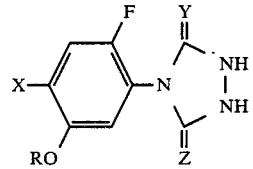

| X | Y | Z | R | Physical property |
|---|---|---|---|---|
| Cl | O | O | —CH₃ | M.P. 223–224° C. |
| Cl | S | O | —CH₃ | Glassy; IR $\nu_{max}$ (cm$^{-1}$): 3160, 1720 |
| Cl | O | O | —CH₂CH₂CH₃ | M.P. 181–182° C. |
| Br | O | O | —CH₃ | M.P. 229–230° C. |

TABLE 2-continued

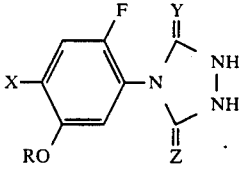

| X | Y | Z | R | Physical property |
|---|---|---|---|---|
| Br | O | O | —CH$_2$CH$_3$ | M.P. 215-216° C. |
| Br | O | O | —CH$_2$CH$_2$CH$_3$ | M.P. 189-189.5° C. |
| Cl | O | O | —CH$_2$C≡CH | M.P. 217-217.5° C. |

EXAMPLE 6

4-Chloro-2-fluoro-5-(1-methylethoxy)phenyl isothiocyanate (2.8 g) was added to a solution of 2-ethoxycarbonyl-3,4,5,6-tetrahydro-(1H, 2H)-pyridazine (1.8 g) and several drops of triethylamine in toluene (5 ml), and the resultant mixture was stirred at 25° C. overnight. Water was added to the mixture, which was then extracted with toluene. The toluene layer was washed with water, dried and concentrated. The residue was purified by silica gel column chromatography to give 2 g of ethyl 2-(4-chloro-2-fluoro-5-(1-methylethoxy)-phenylaminothioxomethyl)-3,4,5,6-tetrahydro-1(2H)pyridazine carboxylate. n$_D^{27.5}$ 1.5534. NMR δ (ppm): 1.3 (3H, t), 1.4 (6H, d), 1.8 (4H, m), 4.35 (2H, q), 7.1 (1H, d), 8.0 (1H, d), 8.45 (1H, m,

).

Some examples of the urea (IV) produced in the same manner as above are shown in Table 3.

TABLE 3

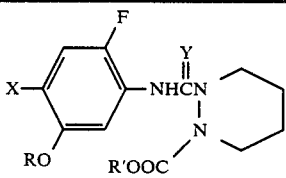

| X | Y | R | R' | Physical property |
|---|---|---|---|---|
| Cl | S | —CH$_3$ | —CH$_2$CH$_3$ | n$_D^{24.0}$ 1.5751 |
| Cl | S | —CH(CH$_3$)$_2$ | —CH$_2$CH$_3$ | n$_D^{27.5}$ 1.5534 |
| Cl | O | —CH$_2$C≡CH | —CH$_2$CH$_3$ | M.P. 135.5-136.5° C. |
| Cl | S | —CH$_2$C≡CH | —CH$_2$CH$_3$ | M.P. 105-109° C. |
| Br | S | —CH$_2$CH$_2$CH$_3$ | —CH$_2$CH$_3$ | Glassy |
| Br | S | —CH$_2$CH=CH$_2$ | —CH$_2$CH$_3$ | M.P. 80-86° C. |
| Br | O | —CH$_2$CH=CH$_2$ | —CH$_2$CH$_3$ | M.P. 77-80° C. |
| Cl | O | —CH$_2$CH$_2$CH$_3$ | —CH$_2$CH$_3$ | n$_D^{25}$ 1.5313 |

EXAMPLE 7

A solution of ethyl 2-(4-chloro-2-fluoro-5-(1-methylethoxy)phenylaminothioxomethyl)-3,4,5,6-tetrahydro-1(2H)pyridazinecarboxylate (0.8 g) in a 5% ethanolic potassium hydroxide solution (10 ml) was heated under reflux for 3 hours. After being allowed to cool to room temperature, ethanol was removed under reduced pressure. The residue was dissolved in ether, washed with water, dried over anhydrous magnesium sulfate and concentrated to give 0.3 g of 2-(4-chloro-2-fluoro-5-(1-methylethoxy)phenylaminothioxomethyl)-3,4,5,6-tetrahydro-(1H,2H)-pyridazine. M.P., 113°-114.5° C.

NMR δ (ppm): 1.35 (6H, d), 1.7 (4H, m), 2.95 (2H, m), 3.45 (1H, t), 4.2 (2H, m), 4.4 (1H, m), 6.95 (1H, d), 8.25 (1H, d), 9.85 (1H, m).

Some examples of the urea (V) produced in the same manner as above are shown in Table 4.

TABLE 4

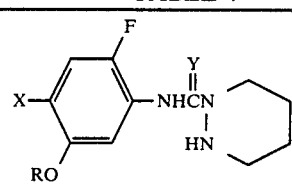

| X | Y | R | Physical property |
|---|---|---|---|
| Cl | S | —CH(CH$_3$)$_2$ | M.P. 113-114.5° C. |
| Cl | O | —CH$_2$CH$_2$CH$_3$ | M.P. 120-122.5° C. |
| Cl | O | —CH$_2$C≡CH | M.P. 89.5-91.5° C. |
| Cl | S | —CH$_2$C≡CH | M.P. 96.5-99° C. |
| Cl | O | —CH$_2$CH=CH$_2$ | M.P. 91-95° C. |
| Br | O | —CH$_2$CH=CH$_2$ | M.P. 80-86° C. |

EXAMPLE 8

A solution of 4-chloro-2-fluoro-5-isopropoxyaniline (30 g) in toluene (100 ml) was added to a 1M phosgene/toluene solution (500 ml) at room temperature (ca. 20° C.), followed by heating under reflux. The mixture was concentrated under reduced pressure, and the residue was distilled to give 26 g of 4-chloro-2-fluoro-5-isopropoxyphenyl isocyanate as pale yellow crystals. M.P., 36°-37° C. B.P., 90°-91° C./3 mmHg.

IR ν$_{max}$ (cm$^{-1}$): 2240.

Some examples of the isocyanate or isothiocyanate (X) produced in the same manner as above are shown in Table 5.

TABLE 5

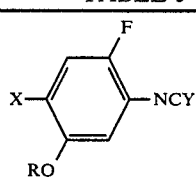

| X | Y | R | Physical property |
|---|---|---|---|
| Cl | O | CH$_3$— | M.P. 42-44.5° C. |
| Cl | O | n-C$_3$H$_7$— | M.P. 43-44° C. |
| Cl | O | iso-C$_3$H$_7$— | M.P. 36-37° C. |
| Br | O | C$_2$H$_5$— | M.P. 35-36.5° C. |
| Cl | O | CH$_2$=CHCH$_2$— | B.P. 107° C./3 mmHg; n$_D^{16}$ 1.5481 |
| Cl | O | CH≡CCH$_2$— | M.P. 61.5-62.5° C. |
| Cl | S | CH$_3$— | M.P. 79-80° C. |
| Cl | S | CH≡CCH$_2$— | M.P. 105-109° C. |
| Cl | S | CH$_2$=CHCH$_2$— | n$_D^{24}$ 1.6228 |
| Br | S | CH≡CCH$_2$— | M.P. 71-74° C. |
| Br | S | CH$_2$=CHCH$_2$— | n$_D^{24}$ 1.6421 |

EXAMPLE 9

A mixture of 4-chloro-2-fluoro-5-isopropoxynitrobenzene (13.5 g) and platinum dioxide (0.4 g) in ethanol (300 ml) was subjected to catalytic reduction with hydrogen at room temperature (ca. 20° C.) under atmospheric pressure, whereby a designed amount of hydrogen was absorbed. The resultant mixture was filtered to remove insoluble materials, and the filtrate was concentrated. The residue was subjected to purification by silica gel chromatography to give 5.6 g of 4-chloro-2-fluoro-5-isopropoxyphenylaniline. n$_D^{24.5}$ 1.5360.

NMR (CDCl₃) δ (ppm): 1.3 (6H, d, J=6 Hz), 3.7 (2H, m, J=1.5 Hz), 4.35 (1H, q, J=6 Hz), 6.45 (1H, d, J=7 Hz), 7.1 (1H, d, J=10 Hz).

IR $\nu_{max}$ (cm⁻¹): 3450, 3550.

EXAMPLE 10

A suspension of electrolytic iron powder (3.5 g) in a 5% aqueous acetic acid solution (5 ml) was heated to 90° C., and a solution of 4-chloro-2-fluoro-5-(2-propynyloxy)nitrobenzene (5.7 g) in acetic acid (40 ml) was dropwise added thereto at the same temperature. The resultant mixture was stirred at 90°–105° C. for 1 hour and allowed to cool to room temperature. Water (200 ml) was added thereto. Insoluble materials were filtered off, and the filtrate was neutralized, followed by extraction with ethyl acetate. The extract was dried over anhydrous magnesium sulfate and concentrated. The residue was washed with petroleum ether and carbon tetrachloride to give 3.6 g of 4-chloro-2-fluoro-5-(2-propynyloxy)aniline. M.P. 61.0°–61.5° C. NMR (CDCl₃) δ (ppm): 2.5 (1H, t, J=2 Hz), 3.4–4.2 (2H, m, J=16 Hz), 4.15 (2H, d, J=2 Hz), 6.5 (1H, d, J=8 Hz), 6.95 (1H, d, J=10 Hz).

IR $\nu_{max}$ (cm⁻¹): 3460, 3360, 3280, 2100.

Some examples of the aniline (IX) produced in the same manner as above are shown in Table 6.

TABLE 6

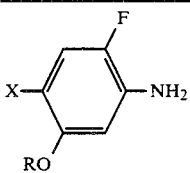

(IX)

| X | R | Physical property |
|---|---|---|
| Cl | C₂H₅— | $n_D^{24.5}$ 1.5503 |
| Br | C₂H₅— | $n_D^{25.0}$ 1.5680 |
| Cl | n-C₃H₇— | $n_D^{24.5}$ 1.5386 |
| Br | n-C₃H₇— | $n_D^{26.0}$ 1.5618 |
| Cl | iso-C₃H₇— | $n_D^{24.5}$ 1.5360 |
| Br | iso-C₃H₇— | $n_D^{25.0}$ 1.5547 |
| Cl | CH₂=CHCH₂— | $n_D^{19}$ 1.5598 |
| Cl | CH≡CCH₂— | M.P. 61.0–61.5° C. |
| Cl | CH≡C—CH—<br>            \|<br>            CH₃ | M.P. 67.0–68° C. |

EXAMPLE 11

To a solution of 2-chloro-4-fluoro-5-nitrophenol (19.1 g) in acetonitrile (100 ml), there was added anhydrous potassium carbonate (8 g). After stirring at room temperature (ca. 20° C.) for several minutes, isopropyl iodide (25 g) was added thereto, and the resultant mixture was heated under reflux for 3 hours. After being allowed to cool to room temperature (ca. 20° C.), water was added thereto, and the reaction mixture was extracted with ether. The ether extract was washed with a 5% aqueous sodium hydroxide solution and water in order, dried over anhydrous magnesium sulfate and filtered. The filtrate was concentrated under reduced pressure, and the residue was recrystallized from ethanol to give 13.5 g of 4-chloro-2-fluoro-5-isopropoxynitrobenzene. M.P., 61.3°–62.4° C.

NMR (CDCl₃) δ (ppm): 1.42 (6H, d, J=7 Hz), 4.3–4.8 (1H, m), 7.28 (1H, d, J=10 Hz), 7.48 (1H, d, J=6 Hz).

Some examples of the nitrobenzene (VIII) produced in the same manner as above are shown in Table 7.

TABLE 7

(VIII)

| X | R | Physical property |
|---|---|---|
| Cl | —CH₃ | M.P. 67.5–69.8° C. |
| Br | —CH₃ | M.P. 72.2° C. |
| Cl | —CH₂CH₃ | M.P. 47–48° C. |
| Br | —CH₂CH₃ | M.P. 46–46.5° C. |
| Cl | —CH₂CH₂CH₃ | M.P. 46–47° C. |
| Br | —CH₂CH₂CH₃ | M.P. 46.8–47.4° C. |
| Cl | —CH(CH₃)₂ | M.P. 61.3–62.4° C. |
| Br | —CH(CH₃)₂ | M.P. 65.5–66.5° C. |
| Cl | —CH(CH₃)CH₂CH₃ | M.P. 59.6–60.6° C. |
| Cl | —CH₂CH=CH₂ | $n_D^{17.0}$ 1.5601 |
| Cl | —CHCH=CH₂<br>   \|<br>   CH₃ | M.P. 41.0–41.5° C. |
| Cl | —CH₂C≡CH | M.P. 88–89° C. |
| Cl | —CHC≡CH<br>  \|<br>  CH₃ | M.P. 87–88° C. |

EXAMPLE 12

2-Chloro-4-fluorophenol (83.4 g) was added to a solution of sodium hydroxide (27.7 g) in water (450 ml), and methyl chloroformate (69.2 g) was dropwise added thereto at a temperature below 10° C. Precipitated crystals were collected by filtration and washed with water to give methyl (2-chloro-4-fluorophenyl)formate (134.8 g). M.P., 69°–71° C.

Methyl (2-chloro-4-fluorophenyl)formate (134.8 g) obtained above was suspended in conc. sulfuric acid (50 ml). To the suspension, a mixture of conc. sulfuric acid (50 ml) and conc. nitric acid (50 ml) was added at about 30° C., and the mixture was stirred at this temperature for 1 hour. The reaction mixture was poured into ice water, and precipitated crystals were collected and washed with water to give methyl (2-chloro-4-fluoro-5-nitrophenyl)formate (143 g). M.P., 50°–55° C.

The product obtained as above was combined with sodium hydroxide (27 g) and water (300 ml), and the resultant mixture was refluxed for 4 hours. Precipitated insoluble materials were filtered using a celite, and the filtrate was acidified with conc. hydrochloric acid. Precipitated crystals were collected by filtration and washed with water to obtain 76.3 g of 2-chloro-4-fluoro-5-nitrophenol. M.P., 106°–107° C.

NMR (CDCl₃, D₆-DMSO) δ (ppm): 7.25 (1H, d, J=10 Hz), 7.64 (1H, d, J=6 Hz).

IR $\nu_{max}^{nujol}$ (cm⁻¹): 3370.

EXAMPLE 13

To a solution of 2-bromo-4-fluorophenol (28 g) in a solution of sodium hydroxide (7 g) in water (100 ml), methyl chloroformate was dropwise added thereto at a temperature below 10° C. The produced crystals were collected by filtration and washed with water to give methyl 2-bromo-4-fluorophenylformate (41 g). M.P., 80.7° C.

The above product was suspended in conc. sulfuric acid (13 ml), a mixture of conc. sulfuric acid (13 ml) and conc. nitric acid (13 ml) was dropwise added thereto at about 30° C., and the resultant mixture of stirred for 30 minutes. The reaction mixture was poured into ice water. The produced crystals were collected by filtration and washed with water to give methyl 2-bromo-4-fluoro-5-nitroformate (38.3 g) as yellow crystals. M.P., 63.5°-64.5° C.

The thus obtained product was admixed with sodium hydroxide (6.2 g) and water (100 ml) and heated under reflux for 3 hours. The insoluble materials were eliminated by filtration, and the filtrate was acidified with hydrochloric acid. The precipitated crystals were collected by filtration and washed with water to give 25 g of 2-bromo-4-fluoro-5-nitrophenol. M.P., 126°-127° C.

NMR (CDCl$_3$, D$_6$-DMSO) δ (ppm): 7.42 (1H, d, J=10 Hz), 7.65 (1H, d, J=6 Hz).

IR $\nu_{max}^{nujol}$ (cm$^{-1}$): 3450.

In the practical usage of the condensed phenylurazols (I), they may be applied as such or in any composition form such as emulsifiable concentrates, wettable powders, suspensions, granules or fine granules.

The concentration of the active ingredient in such composition form is usually within a range of 0.1 to 90% by weight, preferably of 1 to 80% by weight.

For formulation of those compositions, a solid or liquid carrier or diluent may be used. As the solid carrier or diluent, there may be employed mineral powders (e.g. kaolin clay, bentonite, talc, diatomaceous earth, sericite, synthetic hydrated silicon dioxide). As the liquid carrier or diluent, there may be employed aromatic hydrocarbons (e.g. xylene, methylnaphthalene), ketones (e.g. cyclohexanone, isophorone), chlorobenzene, dimethylformamide, cellosolve, ethylene glycol, water, etc.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. If necessary, gelatin, casein, sodium alginate, starch, agar, polyvinyl alcohol, ligninsulfonates, isopropyl acid phosphate, alginates or the like may be used as an auxiliary agent.

Practical embodiments of the herbicidal composition according to the invention are illustratively shown in the following examples wherein part(s) and % are by weight. The compound number of the active ingredient corresponds to the one in Table 1.

FORMULATION EXAMPLE 1

Eighty parts of Compound No. 10, 3 parts of alkylsulfate, 2 parts of ligninsulfonate and 15 parts of synthetic hydrated silicon dioxide are well mixed while being powdered to obtain a wettable powder.

FORMULATION EXAMPLE 2

Twenty parts of Compound No. 14, 10 parts of polyoxyethylene alkylaryl ether, 50 parts of cyclohexanone and 20 parts of xylene are well mixed while being powdered to obtain an emulsifiable concentrate.

FORMULATION EXAMPLE 3

0.1 Part of Compound No. 10, 1 part of synthetic hydrated silicon dioxide, 35 parts of bentonite and 63.9 parts of kaolin clay are well mixed while being powdered. The mixture is then kneaded with water, granulated and dried to obtain granules.

FORMULATION EXAMPLE 4

Three parts of Compound No. 1, 0.3 part of isopropyl acid phosphate, 66.7 parts of kaolin clay and 30 parts of talc are well mixed while being powdered to obtain a dust.

FORMULATION EXAMPLE 5

Eighty parts of Compound No. 3, 5 parts of polyoxyethylene alkylaryl ether and 15 parts of synthetic hydrated silicon dioxide are well mixed while being powered to obtain a wettable powder.

FORMULATION EXAMPLE 6

Ten parts of Compound No. 10, 7 parts of polyoxyethylene alkylaryl ether, 3 parts of alkylarylsulfate and 80 parts of cyclohexanone are well mixed while being powdered to obtain an emulsifiable concentrate.

FORMULATION EXAMPLE 7

One part of Compound No. 9, 1 part of synthetic hydrated silicon dioxide, 5 parts of ligninsulfonate and 93 parts of kaolin clay are well mixed while being powdered. The mixture is then kneaded with water, granulated and dried to obtain granules.

FORMULATION EXAMPLE 8

Three parts of Compound No. 3, 0.5 part of isopropyl acid phosphate, 66.5 parts of kaolin clay and 30 parts of talc are well mixed while being powdered to obtain a dust.

FORMULATION EXAMPLE 9

Twenty parts of Compound No. 9 is mixed with 60 parts of an aqueous solution containing 3% polyoxyethylene sorbitan monooleate and pulverized until the particle size of the active ingredient becomes less than 3 microns. Twenty parts of an aqueous solution containing 3% of sodium alginate as a dispersing agent are incorporated therein to obtain a suspension.

The dosage rate of the condensed phenylurazols (I) may vary depending upon the application mode such as pre-emergence treatment or post-emergence treatement, etc. Generally, however, the dosage rate is from 0.1 to 50 grams, preferably from 0.2 to 30 grams, of the active ingredient per are. Besides, the condensed phenylurazols (I) of the invention may be used together with other herbicides to improve thcir activity as herbicides, and in some cases, a synergistic effect can be expected.

The application of the condensed phenylurazols (I) as herbicides will be illustratively shown in the following Examples wherein the phytotoxicity to crop plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100;

and the phytotoxicity and the herbicidal activity were evaluated by the standard given in the table below.

| Rating value | Fresh weight (percentage to untreated plot) (%) | |
|---|---|---|
| | Herbicidal activity | Phytotoxicity |
| 0 | 61– | 100 |
| 1 | 41–60 | 90–99 |
| 2 | 21–40 | 80–89 |
| 3 | 11–20 | 60–79 |
| 4 | 1–10 | 40–59 |
| 5 | 0 | 0–39 |

The following compounds were used in the Examples for comparison:

| Compound No. | Structure | Remarks |
|---|---|---|
| (a) | Cl-phenyl-N-N(piperidine)(C=O)(C=O) | U.S. Pat. No. 4,249,934 |
| (b) | Cl-(F)phenyl-N-N(piperidine)(C=O)(C=O) | Japanese Patent Publn. (unexamined) No. 44587/78 |
| (c) | Cl-phenyl-N-N(7-ring)(C=O)(C=O) | U.S. Pat. No. 4,249,934 |
| (d) | 2,6-diethylphenyl-N(CH$_2$OCH$_3$)(COCH$_2$Cl) | Commercially available herbicide known as "Alachlor" |
| (e) | triazine with Cl, NHCH(CH$_3$)$_2$, NHC$_2$H$_5$ | Commercially available herbicide known as "Atrazine" |
| (f) | NC-phenyl(3,5-diiodo)-4-OH | Commercially available herbicide known as "Ioxynil" |
| (g) | 2,4-dichlorophenyl-O-phenyl(3-OCH$_3$, 4-NO$_2$) | Commercially available herbicide known as "Chlormethoxynil" |

TEST EXAMPLE 1

Plastic beakers (diameter, 10 cm; height, 10 cm) were filled with upland field soil, and the seeds of barnyardgrass, wild oat, tall morningglory and velvetleaf and the seeds of soybean, cotton and corn were separately sowed in the beakers. A designed amount of the test compound formulated into an emusifiable concentrate according to Formulation Example 2 or 6 and dispersed in water was sprayed over the top by means of a small hand sprayer at a spray volume of 5 liters per are. After the spraying, the test plants were grown for 20 days in the greenhouse, and herbicidal activity and phytotoxicity were examined. The results are shown in Table 8.

TABLE 8

| Compound No. | Dosage (weight of active ingredient, g/are) | Herbicidal activity | | | | Phytotoxicity | | |
|---|---|---|---|---|---|---|---|---|
| | | Barnyard-grass | Wild oat | Tall morningglory | Velvet-leaf | Soybean | Cotton | Corn |
| 1 | 5 | 5 | 5 | 5 | 5 | — | — | — |
|   | 2.5 | 5 | 5 | 5 | 5 | 1 | — | 1 |
| 2 | 5 | 5 | 5 | 5 | 5 | — | — | — |
|   | 2.5 | 5 | 5 | 5 | 5 | — | — | — |
| 3 | 5 | 5 | 5 | 5 | 5 | 1 | — | — |
|   | 2.5 | 5 | 5 | 5 | 5 | 0 | — | — |
| 4 | 5 | 5 | 5 | 4 | 5 | 0 | — | — |
| 6 | 5 | 5 | 5 | 5 | 5 | — | — | — |
|   | 2.5 | 5 | 5 | 5 | 5 | 1 | 1 | — |
| 8 | 5 | 5 | 5 | 5 | 5 | 1 | — | — |
|   | 2.5 | 5 | 5 | 4 | 5 | 0 | — | — |
| 9 | 5 | 5 | 4 | — | 5 | 0 | — | — |
| 10 | 5 | 5 | 5 | 5 | 5 | — | — | — |
|   | 2.5 | 5 | 5 | 5 | 5 | 0 | 0 | — |
| 12 | 5 | 5 | 5 | 5 | 5 | 1 | 1 | — |
|   | 2.5 | 5 | 4 | 4 | 5 | 1 | 0 | — |
| 14 | 5 | 5 | 5 | 5 | 5 | — | — | — |
|   | 2.5 | 5 | 4 | 5 | 5 | 2 | — | — |
| 16 | 5 | 5 | 5 | 5 | 5 | — | — | — |
|   | 2.5 | 5 | 4 | 5 | 5 | — | — | — |

TABLE 8-continued

| Compound No. | Dosage (weight of active ingredient, g/are) | Herbicidal activity | | | | Phytotoxicity | | |
|---|---|---|---|---|---|---|---|---|
| | | Barnyard-grass | Wild oat | Tall morningglory | Velvet-leaf | Soybean | Cotton | Corn |
| 17 | 5 | 5 | 5 | 5 | 5 | — | — | — |
| | 2.5 | 4 | 4 | 5 | 5 | — | — | — |
| 18 | 5 | 5 | 5 | 5 | 5 | — | — | — |
| | 2.5 | 5 | 5 | 5 | 5 | — | — | — |
| (a) | 5 | 1 | 0 | 0 | 3 | — | — | — |
| | 2.5 | 0 | 0 | 0 | 1 | 0 | 1 | 0 |
| (b) | 5 | 3 | 1 | 3 | 5 | — | — | — |
| | 2.5 | 1 | 0 | 2 | 3 | 2 | 3 | 1 |
| (c) | 5 | 1 | 1 | 0 | 4 | — | — | — |
| | 2.5 | 0 | 0 | 0 | 1 | 0 | 0 | — |

TEST EXAMPLE 2

In plastic pots (diameter, 10 cm; height, 10 cm) filled with upland field soil, the tubers of purple nutsedge were transplanted and cultivated in a greenhouse for 4 weeks. Separately, the seeds of barnyardgrass, wild oat, wild mustard and velvetleaf were sowed in the similar pots and grown for 2 weeks in the greenhouse. A designed amount of the test compound formulated in a emulsifiable concentrate according to Formulation Example 2 or 6 and dispersed in water with a spreading agent was sprayed to the foliage of the test plants by means of a small hand sprayer at a spray volume of 5 liters per are. After the spraying, the test plants were further grown for 3 weeks in the greenhouse, and the herbicidal activity was examined. The results are shown in Table 9.

Among the test plants, purple nutsedge was further grown for 2 weeks in the greenhouse, and the number of revived sprouts in the treated plot was compared with that in the untreated plot. Evaluation was made on the following criteria: A, no revival; B, 1 to 10% revival; C, 11–50% revival; D, more than 51% revival. The results are also shown in Table 9.

TABLE 9

| Compound No. | Dosage (weight of active ingredient, g/are) | Herbicidal activity | | | | Prevention of revival Purple nutsedge |
|---|---|---|---|---|---|---|
| | | Barn-yard-grass | Wild oat | Wild mustard | Vel-vet-leaf | |
| 1 | 5 | 4 | 5 | 5 | 5 | A |
| | 1.25 | 3 | 3 | 4 | 5 | — |
| 2 | 5 | 4 | 5 | 5 | 5 | — |
| | 1.25 | 3 | 3 | 5 | 5 | — |
| 3 | 20 | — | — | — | — | A |
| | 5 | 5 | 4 | 5 | 5 | — |
| | 1.25 | — | — | 5 | 5 | — |
| 4 | 5 | 5 | 4 | 5 | 5 | — |
| 6 | 5 | 5 | 5 | 5 | 5 | A |
| | 1.25 | 2 | 3 | 3 | 5 | — |
| 8 | 20 | — | — | — | — | A |
| | 5 | 5 | 5 | 5 | 5 | — |
| | 1.25 | — | — | 5 | 5 | — |
| 9 | 20 | — | — | — | — | A |
| | 5 | 5 | 5 | 5 | 5 | — |
| 10 | 5 | 5 | 5 | 5 | 5 | A |
| | 1.25 | 2 | 2 | •4 | 5 | — |
| 12 | 20 | — | — | — | — | B |
| | 5 | 5 | 4 | 4 | 5 | — |
| 14 | 5 | 4 | 4 | 4 | 5 | A |
| | 1.25 | 2 | 2 | 3 | 5 | — |
| 16 | 5 | 5 | 4 | 5 | 5 | — |
| | 1.25 | 3 | 3 | 5 | 5 | — |
| 17 | 5 | 5 | 4 | 5 | 5 | — |
| | 1.25 | 4 | 3 | 5 | 5 | — |
| 18 | 20 | 5 | 5 | 5 | 5 | A |
| | 5 | 5 | 5 | 5 | 5 | A |
| | 1.25 | 5 | 5 | 5 | 5 | — |
| (a) | 5 | 0 | 0 | 1 | 4 | — |
| | 1.25 | 0 | 0 | 0 | 2 | — |
| (b) | 5 | 1 | 1 | 2 | 5 | D |
| | 1.25 | 0 | 0 | 0 | 3 | — |
| (c) | 5 | 0 | 0 | 1 | 4 | — |

TEST EXAMPLE 3

Plastic trays (35 cm × 25 cm × 15 cm) were filled with upland field soil, and the seeds of tall morningglory, velvetleaf, prickly sida, jimsonweed, back nightshade, redroot pigweed, johnsongrass and green foxtail, and the seeds of cotton and soybean were sowed therein. A designed amount of the test compound formulated into a wettable powder according to formulation Example 1 or 5 and dispersed in water was sprayed over the top by means of a small hand sprayer at a spray volume of 5 leters per are. After the spraying, the test plants were grown in a greenhouse for 20 days, and phytotoxicity and herbicidal activity were examined. The results are shown in Table 10.

TABLE 10

| Compound No. | Dosage (weight of active ingredient, g/are) | Herbicidal activity | | | | | | | | Phytotoxicity | |
|---|---|---|---|---|---|---|---|---|---|---|---|
| | | Tall morning-glory | Velvet-leaf | Prickly sida | Jimson-weed | Black night-shade | Redroot pigweed | Johnson-grass | Green foxtail | Cotton | Soybean |
| 3 | 5 | 5 | 5 | 5 | 5 | 5 | 5 | 5 | 5 | 1 | — |
| | 2.5 | 4 | 5 | 5 | 5 | 5 | 5 | 5 | 5 | 0 | — |
| 10 | 5 | 5 | 5 | 5 | 5 | 5 | 5 | 5 | 5 | 1 | 1 |
| | 2.5 | 4 | 5 | 5 | 5 | 5 | 5 | 4 | 5 | 0 | 0 |
| (a) | 5 | 0 | 4 | 2 | 0 | 3 | 5 | 0 | 2 | — | 0 |
| (b) | 5 | 2 | 5 | 4 | 3 | 5 | 5 | 2 | 4 | 3 | 2 |
| | 2.5 | 0 | 4 | 3 | 1 | 4 | 5 | 0 | 2 | 2 | 0 |
| (c) | 5 | 0 | 5 | 2 | 0 | 4 | 5 | 0 | 2 | 0 | — |

TABLE 10-continued

| Compound No. | Dosage (weight of active ingredient, g/are) | Herbicidal activity ||||||||| Phytotoxicity ||
| --- | --- | --- | --- | --- | --- | --- | --- | --- | --- | --- | --- |
| | | Tall morning-glory | Velvet-leaf | Prickly sida | Jimson-weed | Black night-shade | Redroot pigweed | Johnson-grass | Green foxtail | Cotton | Soybean |
| (d) | 20 | 1 | 0 | 2 | 0 | 4 | 5 | 2 | 5 | 0 | 0 |

TEST EXAMPLE 4

Plastic trays (35 cm × 25 cm × 15 cm) were filled with upland field soil, and the seeds of corn, wheat, velvetleaf, cocklebur, tall morningglory, common lambsquarters, black nightshade, common chickweed and green foxtail were sowed and grown for 2 to 3 weeks in a greenhouse. Every two trays were placed in a frame (50 cm × 100 cm × 40 cm) and a designed amount of the test compound was sprayed thereover by means of a small hand sprayer. The test plants were further grown for 3 weeks in the greenhouse and herbicidal activity and phytotoxicity were examined. The results are shown in Table 11. In this treatment, the test compound was formulated into an emulsifiable concentrate according to Formulation Example 2 and applied by diluting it in water (25 liters) with the addition of a spreading agent. At the time of application, the plants were generally at the 1 to 4 leaf stage and at a height of 1.5 to 20 cm.

TABLE 11

| Compound No. | Dosage (weight of active ingredient, g/are) | Phytotoxicity || Herbicidal activity |||||||
| --- | --- | --- | --- | --- | --- | --- | --- | --- | --- |
| | | Corn | Wheat | Velvet-leaf | Cock-lebur | Tall morning-glory | Common lambs-quarters | Black night-shade | Common chick-weed | Green fox-tail |
| 1 | 0.63 | 1 | 1 | 5 | 5 | 5 | 5 | 5 | 4 | 3 |
| | 0.32 | 1 | 0 | 5 | 5 | 5 | 5 | 4 | 3 | 2 |
| 14 | 0.63 | — | 1 | 5 | 5 | 5 | 5 | 5 | 4 | 4 |
| | 0.32 | 1 | 1 | 5 | 5 | 5 | 5 | 5 | 2 | 2 |
| (e) | 2.5 | 0 | — | 5 | 5 | 5 | — | — | — | 1 |
| | 1.25 | 0 | — | 4 | 3 | 3 | — | — | — | 0 |
| (f) | 2.5 | — | 0 | — | — | — | 5 | 5 | 5 | 0 |
| | 1.25 | — | 0 | — | — | — | 5 | 4 | 3 | 0 |

TEST EXAMPLE 5

Wagner's pots (1/5000 are) were filled were paddy field soil and the seeds of annual weeds (e.g. barnyardgrass, monchoria, broad-leaved weeds) were sowed to 2 to 3 cm depth, and water was poured therein. The tubers or buds of perennial weeds (e.g. slender spikerush, hardstem bulrush, arrowhead) were transplanted therein and grown for 5 days. At the time when the germination occurred, a designed amount of the test compound formulated in an emulsifiable concentrate according to Formulation Example 2 or 6 was applied to the pots by perfusion. Thereafter, the test plants were grown for an additional 4 weeks and herbicidal activity was examined. The results are shown in Table 12.

TABLE 12

| Compound No. | Dosage (weight of active ingredient, g/are) | Herbicidal activity ||||||
| --- | --- | --- | --- | --- | --- | --- | --- |
| | | Barnyard-grass | Monochoria | Broad-leaved weed | Slender spikerush | Hardstem bulrush | Arrow-head |
| 9 | 0.5 | 5 | 5 | 5 | 5 | 5 | 5 |
| | 0.25 | 4 | 5 | 5 | 4 | 4 | 4 |
| 14 | 0.5 | 5 | 5 | 5 | 5 | 5 | 5 |
| | 0.25 | 4 | 5 | 5 | 4 | 4 | 4 |
| (a) | 0.5 | 0 | 3 | 3 | 1 | 1 | 0 |
| | 0.25 | 0 | 1 | 1 | 0 | 0 | 0 |
| (b) | 0.5 | 0 | 3 | 3 | 2 | 1 | 0 |
| | 0.25 | 0 | 2 | 1 | 1 | 0 | 0 |
| (c) | 0.5 | 0 | 3 | 2 | 1 | 2 | 1 |
| | 0.25 | 0 | 2 | 1 | 0 | 0 | 0 |
| (g) | 0.5 | 2 | 2 | 2 | 2 | 1 | 1 |
| | 0.25 | 1 | 2 | 2 | 1 | 0 | 0 |

What is claimed is:

1. A condensed phenylurazol of the formula:

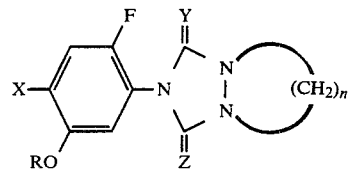

wherein X is a chlorine atom or a bromine atom, Y and Z are each an oxygen atom or a sulfur atom and R is a $C_1$-$C_3$ alkyl group, an allyl group or a propargyl group and n is 5.

2. The condensed phenylurazol according to claim 1, wherein at least one of Y and Z is an oxygen atom.

3. A condensed phenylurazol compound according to claim 1, wherein X is a chlorine atom.

4. A condensed phenylurazol formula according to claim 3, wherein Y and Z are each an oxygen atom.

5. A condensed phenylurazol compound according to claim 1, which is 2-(4-Chloro-2-fluoro-5-methoxyphenyl)-1H,5H-[1,2,4]triazolo[1,2-a][1,2]diazepine-1,3(2H)-dione.

6. A condensed phenylurazol compound according to claim 4, wherein R is an n-propyl group.

7. A condensed phenylurazol compound according to claim 3, wherein both Y and Z are each a sulphur atom.

8. A condensed phenylurazol compound according to claim 7, wherein R is a methyl group.

9. A condensed phenylurazol compound according to claim 1, wherein X is a bromine atom.

10. A condensed phenylurazol compound according to claim 9, wherein Y and Z are each an oxygen atom.

11. A condensed phenylurazol compound according to claim 10, wherein R is an ethyl group.

12. A condensed phenylurazol compound according to claim 9, wherein Y and Z are each a sulphur atom.

13. A condensed phenylurazol compound according to claim 12, wherein R is an ethyl group.

14. A herbicidal composition which comprises a herbicidally effective amount of the condensed phenylurazol according to claim 1 and an inert carrier.

15. A method for controlling or exterminating weeds which comprises applying a herbicidally effective amount of the condensed phenylurazol according to claim 1 to the area where the weeds grow or will grow.

16. A herbicidal composition which comprises a herbicidally effective amount of the condensed phenylurazol compound according to claim 5 and an inert carrier.

17. A herbicidal composition which comprises a herbicidally effective amount of the condensed phenylurazol compound according to claim 8 and an inert carrier.

18. A herbicidal composition which comprises a herbicidally effective amount of the condensed phenylurazol compound according to claim 11 and an inert carrier.

19. A herbicidal composition which comprises a herbicidally effective amount of the condensed phenylurazol compound according to claim 13 and an inert carrier.

* * * * *